United States Patent [19]

Funke

[11] Patent Number: 5,113,859

[45] Date of Patent: May 19, 1992

[54] ACOUSTIC BODY BUS MEDICAL DEVICE COMMUNICATION SYSTEM

[75] Inventor: Hermann D. Funke, Bonn, Fed. Rep. of Germany

[73] Assignee: Medtronic, Inc., Minneapolis, Minn.

[21] Appl. No.: 543,611

[22] Filed: Jun. 25, 1990

Related U.S. Application Data

[63] Continuation-in-part of Ser. No. 408,811, Sep. 18, 1989, Pat. No. 4,987,897.

[30] Foreign Application Priority Data

Sep. 19, 1988 [DE] Fed. Rep. of Germany ....... 3831809

[51] Int. Cl.⁵ .......................................... A61N 1/362
[52] U.S. Cl. ........................ 128/419 PG; 128/419 D
[58] Field of Search ........... 128/419 R, 419 PG, 419 D

[56] References Cited

U.S. PATENT DOCUMENTS

| | | | |
|---|---|---|---|
| 4,146,029 | 3/1979 | Ellinwood | 128/260 |
| 4,494,950 | 1/1985 | Fischell | 128/635 |
| 4,531,527 | 7/1985 | Reinhold, Jr. et al. | 128/696 |
| 4,787,389 | 11/1988 | Tarjan | 128/419 |
| 4,886,064 | 12/1989 | Strandberg | 128/419 |
| 4,987,897 | 1/1991 | Funke | 128/419 PG |
| 4,989,602 | 2/1991 | Sholder et al. | 128/419 |

Primary Examiner—William E. Kamm
Assistant Examiner—Scott M. Getzow
Attorney, Agent, or Firm—John A. Rissman; Harold R. Patton

[57] ABSTRACT

A system intended for being at least partly implanted into a living body and comprising at least two modules or devices which are interconnected by a communication transmission channel, at least one of said modules being provided with transmitting and receiving means for a bidirectional exchange of information with at least one further module and at least one other module of which being provided at least with receiving means or transmitting means for receiving information from at least one further module or for transmitting information to at least one further module, respectively. Within the intracorporeal region, said communication transmission channel by data modulated ultrasound. The body mass provides for an ultrasonic coupling between two or more implantable modules and/or between at least one implantable module and an external skin transducer intended for connection to an external module. The exchange of information is effected by modulated medium frequency signals in the frequency range from 10 to 100 kHz, which signals are passed through said communication transmission channel and transmitted or received by ultrasonic transducers, e.g. piezoelectric crystals.

3 Claims, 5 Drawing Sheets

ACOUSTIC BODY BUS MEDICAL DEVICE COMMUNICATION SYSTEM

This application is a continuation-in-part of my commonly assigned, copending U.S. patent application Ser. No. 07/408,811, filed Sep. 18, 1989, now U.S. Pat. No. 4,987,897 which application claims priority from German Patent Application No. P 38 31 809.1, filed Sep. 19, 1988.

BACKGROUND OF THE INVENTION

1. Field of the Invention

This invention relates to a system of medical devices intended for being at least partly implanted into a living body and comprising at least two modules which are interconnected by a communication transmission channel denoted the "ultrasonic body bus".

2. Description of the Prior Art

In my aforementioned U.S. patent application Ser. No. 07/408,811, I set forth the prior art to the transmission of electrical signals by wireless transmissions between electrodes in the body or on the body surface. This application differs in that acoustic signal transmissions within the body or on the body surface are contemplated in the present invention. Thus the following prior art is applicable to that related invention.

Devices employing radio frequency communication which are known in different embodiments, e.g. EPO 0 011 935 and EPO 0 011 936, which describe an external programming device and an implantable electromedical device adapted for being programmed thereby, wherein the programming device comprises a transmitting antenna, and the implantable device comprises a receiving antenna which are mutualy aligned with each other for programming in order to transcutaneously transmit high radio frequency programming signals in the form of electromagnetic waves from the transmitting antenna to the receiving antenna. In view of the fact that high frequency electromagnetic waves are heavily attenuated or screened by body tissue, the implanted receiving antenna must be exactly located for programming. Such a procedure is particularly troublesome if a plurality of programmable modules, e.g. a pacemaker, a defibrillator and a drug dispensing device, are implanted, the receiving antennas of which must be individually located.

In the case of a prior muscle stimulation apparatus (U.S. Pat. No. 4,524,774) in a similar manner, muscle potentials detected by implanted sensors are converted by a modulator into control signals for a radio frequency telemetry transmitter which is integrated into the respective sensor. This telemetry transmitter transcutaneously transmits high frequency telemetry signals to an external telemetry receiver which is connected to a data processing unit. The latter, on the base of the received signals, controls a likewise externally disposed telemetry transmitter for delivering high frequency control signals, against transcutaneously, to receivers of implanted muscle stimulators. The transcutaneously transmitted signals are in the megacycles/sec. frequency range so that the aforementioned restrictions are encountered in this case too.

Furthermore, it is known (FIG. 1 of U.S. Pat. No. 4,543,955) to transmit measuring signals of an implanted sensor module through a wire connection to another implanted module, such as a pacemaker or a drug delivery device. This requires, during implantation, a troublesome wiring of connection conduits. Furthermore if an infection occurs at one of the implanted modules, all modules and connection conduits must be removed because the infection can spread along the connection conduits. In conformity with modified embodiments of the last mentioned device (FIGS. 2 and 5 of U.S. Pat. No. 4,543,955) measuring signals, which have been converted into a program code, also can be unidirectionally transmitted, in a wireless manner, from the sensor to the pacemaker or to the drug dispensing device, wherein either the signals defining the program code are directly transmitted through body tissue (i.e., without any carrier) or again a high frequency transmitter is used. A carrier free signal direct transmission, for being effective, must be carried through during the refractory phases, i.e. must be synchronized with the heart cycle because otherwise the signals required for such a direct transmission may provoke undesired biological reactions. On the other hand, the high frequency transmission, in this case too, poses problems because of the heavy attenuation caused by body tissue and is possible, if at all, merely if the transmitting and receiving antennas are closely spaced with in the body.

In addition, it is known from U.S. Pat. No. 4,787,389 to provide implantable defibrillator-pacemaker system where the defibrillator's operation is controlled by the separately implanted pacemaker. Signal transmission is effected by coded pulse trains as in U.S. Pat. No. 4,593,955.

In regard to the present invention, it is known to employ piezoelectric transducers within body implantable devices in order to transform body activity into energy to power the circuitry of the device or to develop a pacing rate control signal. The U.S. Pat. No. 3,456,134 illustrates an example of the former concept wherein a piezoelectric crystal mounted in pendulum fashion vibrates with body activity to generate electrical current which is rectified and stored to power a circuit. My article, "Ein Herzschrittmacher mit belastungsabhaengiger Frequenzregulation" (A Cardiac Pacemaker with Activity-Dependent Frequency Regulation); Biomedizinsche Technik, Band 20, Heft 6.75, describes the use of a piezoelectric crystal respiratory frequency detector for varying pacing rate as a function of respiration rate. More recently, U.S. Pat. No. 4,428,378 discloses the use of a piezoelectric crystal sensor mounted against the interior surface of a pacemaker case for detecting the frequency of muscle activity and deriving a pacing rate control signal. Such activity responsive physiologic pacemakers have been widely sold in recent years.

However, the concept of using piezoelectric crystals to provide intracorporeal and/or extracorporeal body surface data communication and signalling is not known from this prior art.

SUMMARY OF THE INVENTION

The object basic to the invention is to provide for a device of the type mentioned at the beginning which allows a signal transmission between the modules in a particularly simple, reliable and universally applicable manner while simultaneously avoiding the above discussed deficiencies.

In conformity with the invention, this object is reached by a system intended for being at least partly implanted into a living body and comprising at least two medical devices or modules which are interconnected by an ultrasound communication transmission channel, at least one of said modules being provided with transmitting and receiving ultrasound transducer means for a bidirectional exchange of information with at least one further module and at least one other module of which being provided at least with ultrasound transducer receiving means or transmitting means for receiving information from at least one further module or for transmitting information to at least one further module, respectively, wherein within the intracorporal region said communication transmission channel is wireless and provides for an ultrasound wave transmission between two or more implantable modules and/or between at least one implantable module and external skin ultrasound transducer intended for connection to an external module and wherein the exchange of information is effected by modulated medium frequency ultrasound signals in the carrier frequency range from 10 to 100 kHz, which signals are passed through said communication transmission channel by direct acoustic wave conduction.

A modulated ultrasound signal in the frequency range from 10 kHz to 100 kHz has a sufficiently high frequency to not cause any problems with audio hearing and to allow an effective filtering with high Q filters requiring only little installation space. On the other hand, this frequency range is so low that undesired high frequency phenomena, such as radiation problems, crosstalk and excessive attenuation of the desired signals by the body tissue are avoided. Rather, modulated signals in the frequency range from 10 to 100 kHz can be acoustically transmitted over the relatively short distances encountered in the living body with such a low attenuation that, on the transmitter side, signal amplitudes which biologically are certainly ineffective and which can be transmitted without any regard to the heart cycle can be received by receiver with a piezoelectric crystal sensor (which might also be provided for detecting the patient's activity) with sufficient amplitude allow the modulated signals to be reliably detected at the receiver side at low expenditure for filters and amplifiers, and loss of energy.

A bidirectional exchange of information by such accoustic waves provides for an interactive mutual coupling of the individual modules. The functional interconnection between implanted and external modules may be obtained in a particularly simple manner via body fluids by making use of the acoustic transducer coupling, so that a troublesome search for the prior art antennas of the implanted module or modules is avoided.

In conformity with a further development of the invention, at least one digitally programmable implantable module and an external module in the form of a programming device are provided. The programmer would, because of the body bus bidirectional properties, enable interactive intelligent programming. Over a modem, telephone programming and control would be possible, especially for endangered tachy or defibrillator patients, although the frequency range selected could have to take into account the capabilities of the telephone system.

Preferred examples of implanted modules are nerve stimulators, muscle stimulators, cardiac pacemakers, cardioverters, defibrillators, drug dispensing devices, sensors for detecting body parameters or body activities as well as controllable and/or programmable artificial organs. Apart from the aforementioned programming devices, particularly, but not exclusively, monitoring and/or test devices may be used as external modules such as data recording devices (magnetic tape devices or the like) or models adapted for connection to telephone circuits.

If a plurality of implantable modules are provided, programming and/or intelligent decision means, in conformity with a further development of the invention, preferably are concentrated in one of the implanted modules only wherein, in case of need, other implanted modules can be indirectly programmed via said one module. Thereby it is possible to keep the hardware expenditure, the weight, the space requirements and the energy consumption of the total of implanted modules particularly small. Basically, however, it is likewise possible to provide a plurality of implanted modules comprising programming and/or intelligent decision means which modules mutually communicate via the body bus.

Preferably the modules are provided with means for receiving and/or transmitting of pulsecode-modulated medium frequency signals. A1-modulated medium frequency signals may be used, i.e. the signal has a single, fixed frequency of e.g., 40 kHz, and this signal, at the transmitting side, is switched on and off as a function of the modulation. In conformity with a modified embodiment, the modules may be each provided with a second piezoelectric crystal transducer means for receiving and/or transmitting signals which are frequency shifted between a pair of frequencies within the medium frequency range. For example, a pair of predetermined fixed signal frequencies, e.g. of 30 kHz and 40 kHz may be used, and shifting takes place at the transmitting side between the two signal frequencies and respective transducers as a function of the modulation. The A1 pulsecode modulation avoids sidebands and continuous frequency swings. The one or the two signal frequencies can be generated at the transmitting side by means of crystal oscillators with a high frequency accuracy and high frequency stability whereas at the receiving side, narrow-banded amplifiers which e.g. are provided with crystal filters and which are tuned to the signal frequence or the signal frequencies, may be provided.

The invention has a multiplicity of advantageous applications. For example, tachycardiac rhythm disturbances so far at first are treated with drugs. On further progress of the disease, antibradycardiac stimulation by means of a sequential pacemaker of the type known from German unexamined published patent application 27 01 140 may become necessary, wherein simultaneously or at a later state it may be advantageous to supplement the antibradycardiac stimulation by antitachycardiac stimulation pattern (compare e.g., European Patent Specification 0 094 758). When this too is no longer sufficient to adequately influence the syndrome and attacks of ventricular fibrillation occur, a defibrillator becomes necessary which likewise is available as an implantable device. However, when implanting the defibrillator, the sequential pacemaker again must be explanted because this pacemaker delivers atrial and ventricular stimulating pulses which, in the same manner as possibly the R-wave of the electrocardiogram, too, are detected by the defibrillator whereby the latter sees an apparent frequency duplication or frequency triplication. When the heart works correctly with e.g. 70 beats per minute, therefore, there is the risk that the defibrillator detects an apparent heartbeat rate of 140 or 210 beats per minute and undesirably delivers a defibrillation pulse. When the pacemaker is explanted, necessarily the antibradycardiac and possibly also antitachycardiac protective effect thereof no longer exists. Besides, the drug dosage must be reduced because the patient no longer is protected against a drop of the rate of the heart activity. The defibrillator will become active relatively frequently.

Within the scope of the present invention, it is possible to transfer the intelligent decisions, particularly the detection of the requirement of a defibrillation shock, from the defibrillator to the preferably A-V sequential, programmable, microprocessor based pacemaker and to make the defibrillator only indirectly programmable via the pacemaker making use of the ultrasound body bus. The pacemaker, which may be designed in the manner known from European Patent Specification 0 094 758, safely detects whether the pacemaker itself stimulates or whether there is a tachycardia. When a tachycardia is detected, the pacemaker can request the shock from the defibrillator through the acoustic ultrasound body bus. Therefore, if in the course of the therapy the sequential pacemaker no longer will be sufficient, this pacemaker need not be explanted. Rather the therapy can be systematically built up as a function of the respective requirements without previous implants becoming obsolete. In view of the monitoring functions included in the pacemaker, the requirement of the additional implantation of a defibrillator function can be detected at an early state. The defibrillator, which constitutes a high current application, then can be added. Simultaneously, the sequential, antibradycardial stimulation (possibly assisted by drugs) reduces the fibrillation incidence when compared with a pure ventricular stimulation. The stimulation treatment of tachycardia likewise can be carried through by the pacemaker, optionally in a dual chamber manner, whereby the effectivity of detection and of the treatment is increased thereby again reducing the probability of fibrillation. Thus the defibrillator may be restrained, as far as conceivable, to its function as an emergency or backup system.

With respect to the separation of pacemaker and defibrillator, which is easily possible by making use of the acoustic ultrasound body bus, it is to be taken into consideration that the pacemaker, particularly if, in a manner known per se, it is microprocessor controlled and programmable and also includes antitachycardiac algorithms, constitutes a complex and therefore relatively expensive device which, however, merely has a low current consumption and therefore has a very long duration even if the housing volume, as desired, is small. Besides, the pacemaker may be implanted at many appropriate different body sites. In contrast, a defibrillator has a high energy consumption and, if it was only in view of its storage capacitors, a large volume. It can be implanted at a few body sites only, and in view of its high energy drain, has a relatively short lifetime. Normally it does not make sense to combine the pacemaker and the defibrillator in one and the same casing.

Moreover, recent clinical studies of patients implanted with AICD devices indicate that in a large number of such patients, the defibrillation shock is delivered quite infrequently, i.e. two to four times a year. Despite the infrequent delivery of the shocks, the AICD units need to be replaced within two years due to the deterioration of the batteries. The system of the present invention contemplates the possibility of replacing a large volume, large capacity defibrillator with a small volume low capacity (in other words, a limited number of shocks) in those patients where experience has shown that the patient only infrequently requires a defibrillation shock. It can be expected that in even those patient populations, the frequency of required defibrillation shocks will be diminished by the efficacy of antitachycardia pacing therapies delivered by the separate pacemaker unit.

Thus the present invention contemplates the provision of a staged therapy to the patient first involving the implantation of an intelligent pacemaker in the patient and then, if necessary, the additional implantation of a defibrillator having a shock delivery capacity tailored to the requirements of the patient, e.g. 10, 20, 100 shocks per year at maximum programmable output energy.

In addition, the ultrasound body bus system components may include separate remote sensors for physiologic rate responsive pacing and/or detection of arrhythmias (to augment or replace the electrogram sensing employed to confirm malignant VT or VF) as well as a drug dispenser. The drug may be delivered into the patient's body or the patient's vascular system as is appropriate to treat the patient in a fashion which the pacemaker electronics would find appropriate. For treatment of an arrhythmia detected by the pacemaker, the drug may be delivered into the vascular system or a chamber of the heart or into the body of the patient in conformance with the appropriate delivery of the specific drug.

BRIEF DESCRIPTION OF THE DRAWINGS

These and other additional objects and features of the present invention will become readily apparent when the same are set forth in greater detail in the accompanying detailed description of the preffered embodiments with reference being made to the drawings in which like reference numerals represent like or similar parts throughout and in which.

DESCRIPTION OF THE PREFERRED EMBODIMENTS

Figure 1:
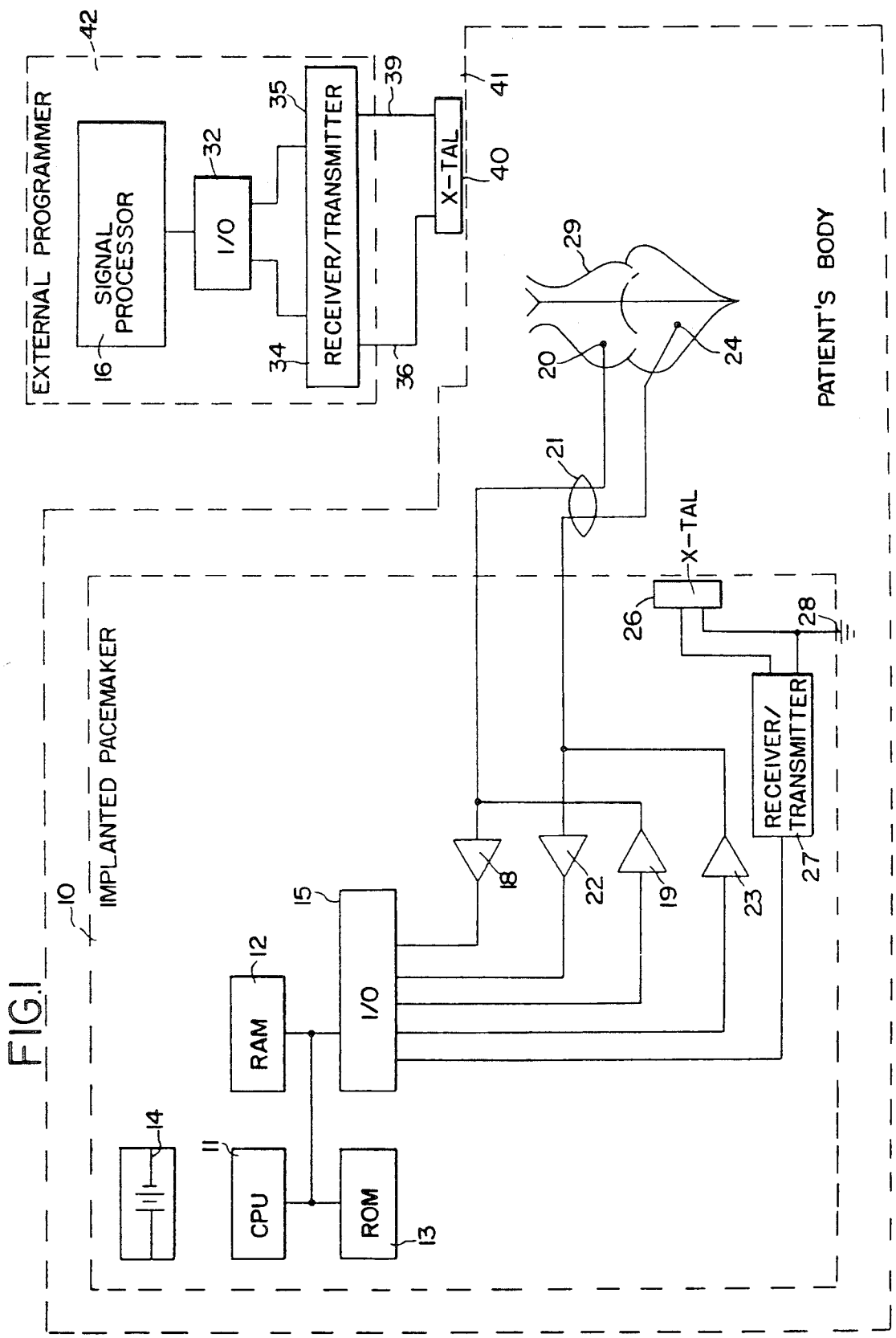
FIG. 1 is a schematic circuit diagram of a cardiac pacemaker adapted for being programmed via the body bus.

FIG. 1 shows an implanted microprocessor controlled, programmable cardiac pacemaker 10 comprising a central processing unit (CPU) 11, a random access memory (RAM) 12, a read-only memory (ROM or EPROM) 13, a battery 14 and an input/output unit (I/O) 15. The input/output unit includes amongst others a coder and a decoder for coding and decoding, respectively, of serial information to be exchanged between the cardiac pacemaker 10 and other implantable or external modules in the illustrated embodiment an external programming unit 42. Such programmable pacemakers and associated programming devices e.g. are known from unexamined published European Patent Application 0 011 935 and European Patent Specification 0 011 936; they, therefore, presently need no further explanation.

The input/output unit 15 is connected through an input or sensing amplifier 18 and an output amplifier 19 to the atrial electrode 20 of a pacemaker lead 21; besides it is connected through an input or sensing amplifier 22 and an output amplifier 23 to a ventricular electrode 24 of the pacemaker lead 21. An acoustic body bus transmitter/receiver 27 and piezoelectric crystal 26 (mounted to the case of the device) is connected to a further input/output of the input/output unit 15.

The programming signal processor 16 is connected via an input/output unit 32 to an acoustic body bus receiver/transmitter 34. Input/output lines 36, 39 of the acoustic body bus receiver/transmitter 34 are connected to piezoelectric crystal 40 which is applied against the skin of the patient. The unit 16, together with units 32 to 35, forms an external programming device 42 having a transmitting and receiving capability defined by the acoustic transducer 40 and receiver/transmitter 34.

Figure 2:
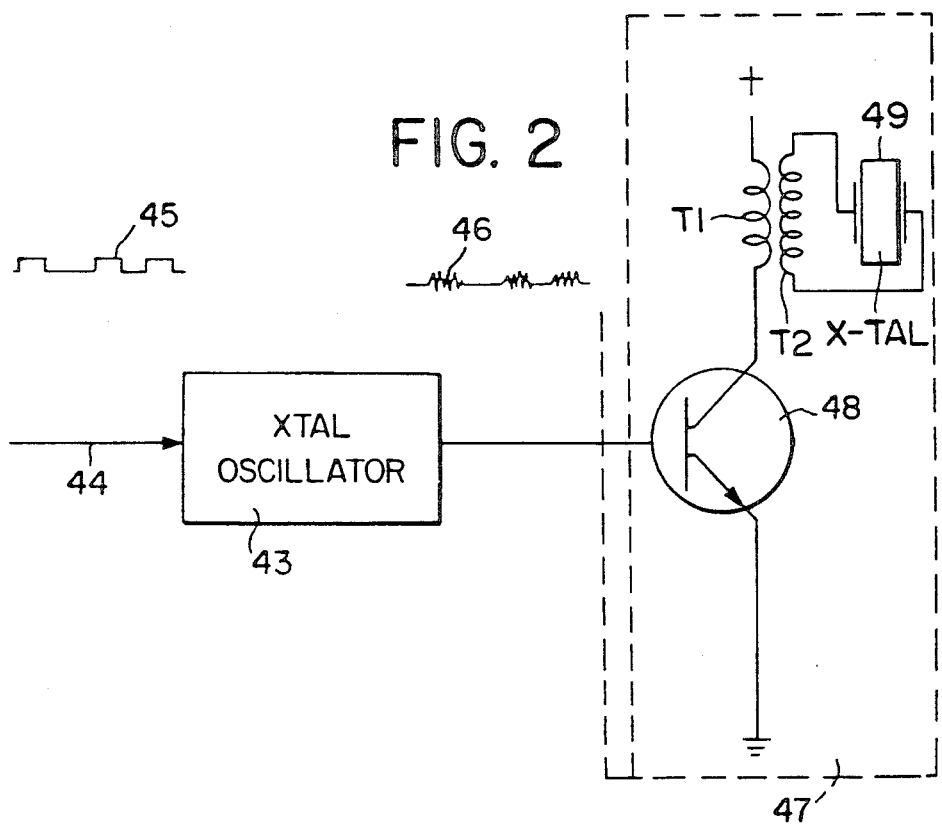
FIG. 2 is a schematic diagram of an ultrasound body bus transmitter.

The acoustic ultrasound body bus transmitters 27, 34 may be designed in the manner illustrated in the schematic circuit diagram of FIG. 2. The transmitter includes an oscillator 43, preferably a crystal oscillator, which generates a preferably sinusoidal carrier signal having a fixed predetermined frequency in the medium frequency range extending from 10 kHz to 100 kHz. The oscillator 43 is keyed, in conformity with a pulse code or A1-modulation, by a serial modulation signal 45 supplied to an input 44. The oscillator correspondingly supplies at its output a modulated medium frequency carrier signal 46 consisting of groups of each a plurality of carrier oscillations. The modulated carrier signal is supplied to the input of an output unit 47 which includes a transistor 48 which delivers across a primary transformer coil T1 to secondary coil T2 and crystal transducer 49 an amplified modulated carrier signal having an amplitude of preferably about 5 volts.

Figure 3:
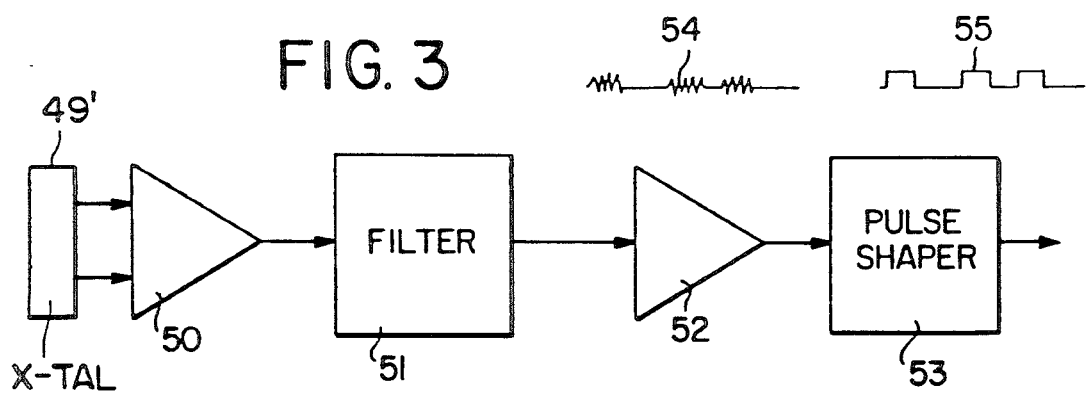
FIG. 3 is a schematic circuit diagram of an ultrasound body bus receiver.

A design suitable for the acoustic ultrasound body bus receivers 26 and 34 schematically is illustrated in FIG. 3. The receiver, at the input side thereof, includes a preamplifier 50, e.g. an amplifier coupled to crystal transducer or microphone 49'. Preamplifier 50 is followed by a high-Q filter 51, preferably a crystal filter, which is tuned to the carrier frequency of e.g. 40 kHz. Filter 51 provides a narrow passband for the carrier signal and substantially suppresses signals of all other frequencies. Filter 51 is followed by a further amplifier unit 52 and a demodulator and pulse shaping unit 53 which converts the received filtered groups of carrier signal oscillations 54 into pulses 55 of predetermined amplitude and a duration defined by the code.

Returning to FIG. 1, in order to program the implanted pacemaker, i.e. for setting or changing parameters such as the rate, the amplitude and the width of the stimulation pulses, the sensitivity of the input amplifiers 18, 22, the refractory period, the detection algorithm for detecting arrhythmias (rate, onset/acceleration, number of intervals to trigger, etc.) and the like and/or for selecting one of a plurality of possible pacemaker modes, the crystal transducer 40 is applied at a desired site of the patient, e.g. in the chest, and serially coded programming commands in the form of the modulated medium frequency carrier signal are supplied to the transducer 40 from the programming unit 42 via the input/output unit 32 and the acoustic body bus receiver/transmitter 34. The transducer 40 transcutaneously introduces the modulated acoustic carrier signal into the body of the patient where the acoustic signal is propagated in the body mass. In this manner, the modulated acoustic carrier signal is transmitted by direct mechanical coupling picked up by crystal 26 to the crystal transmitter/receiver 27 mounted inside the pacemaker 10.

The modulated carrier signal then is amplified, filtered, demodulated and shaped in the body bus receiver/transmitter 26 and is decoded via input/output unit 15 for further processing. In a corresponding manner the programming device 42 can request from pacemaker 10 information for purposes of monitoring, repeating and remote indicating or the like. This information, again in serially coded form, is communicated from the input/output unit 15 to the body bus receiver/transmitter 27 where it modulates a medium frequency carrier signal. The modulated carrier signal is applied to the transmitter/receiver crystal transducer 26 which generates waves transmitted through the body, is propagated there and transcutaneously reaches the external crystal transducer 40 of the programming device 42 which transducer now acts as a microphone. The modulated medium frequency ultrasound signal is filtered out in a narrow band mode, is amplified, demodulated and shaped and finally is processed via decoding in input/output unit 32 for being applied to the signal processor unit 16 for decoding storage and display.

Whereas the transmitters and receivers of FIGS. 2 and 3 are designed for an A1-modulation, other modulation modes, particularly a pulse code modulation with shifting between a pair of carrier signal frequencies and crystal transducers within the frequency range from 10 kHz to 100 kHz (so-called FSK-modulation) likewise can be used for the body bus receiver/transmitters 27, 34, as described above.

Figure 4:
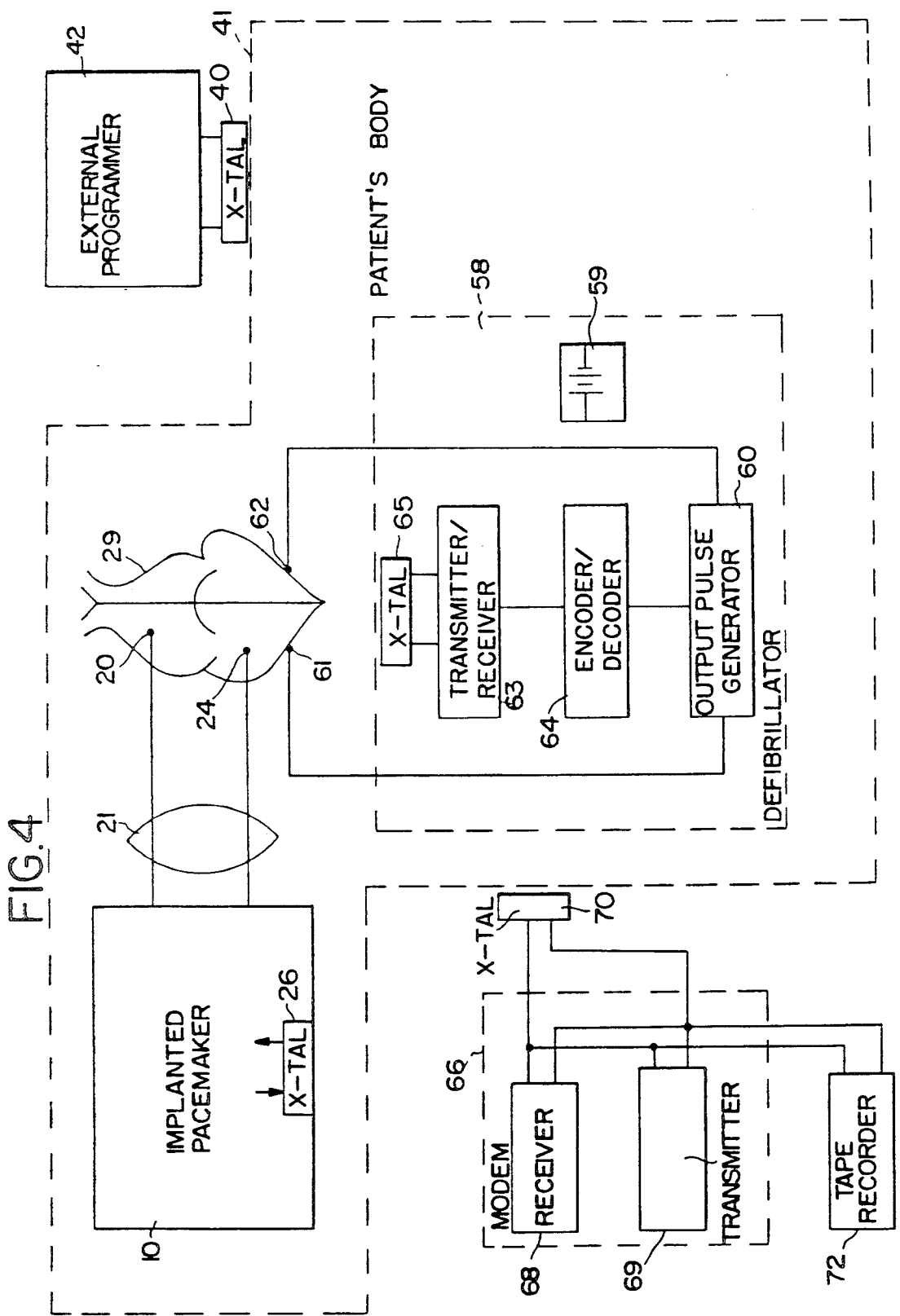
FIGS. 4 and 5 illustrate modified embodiments of devices designed in conformity with the present invention.

The arrangement of FIG. 1, even still at a later date, easily can be further expanded, e.g. by implantation of a defibrillator 58, as schematically illustrated in FIG. 4. The defibrillator 58 comprises a defibrillator output unit 60 adapted to be charged from a battery 59, the output side of unit 60 being connected to implanted defibrillator electrodes 61 and 62. The defibrillator output unit 60, at the input side thereof, is controlled through an acoustic body bus transceiver 63 and an encoder/decoder 64 connected to the output of the latter. The inputs of the acoustic body bus transceiver 63, which e.g. is designed in conformity with FIG. 3, are connected to the crystal transducer 65. The defibrillator 58 together with its associated battery 59 is housed within its own casing, and it can be implanted at a suitable site remote from the pacemaker 10. The crystal transducer 65 is also mounted within the casing, preferably mounted to the interior casing wall.

Defibrillator 58 is controlled by pacemaker 10 which, for this purpose, is provided in a manner known per se (e.g. in conformity with U.S. Pat. No. 4,548,209 and European Patent Specification 0 094 758) with tachycardia and/or fibrillation detection means and, if desired, likewise with means for providing antitachycardiac pacing stimulation pattern, e.g. overdrive, burst or ramp stimulation as is known in the art. In this connection, also means for indirectly programming the defibrillator through the pacemaker 10 and the acoustic ultrasound body bus may be provided. The acoustic ultrasound body bus permits one to intelligently employ the defibrillator 58 which itself does not comprise means for sensing and for making decisions. For example, provisions can be made by a corresponding software design of the microprocessor controlled pacemaker 10 that in case of ventricular tachycardia which cannot be interrupted by means of the pacemaker 10 at first a cardioversion attempt with low energy is caused, whereas in the case of the occurrence of ventricular fibrillation, immediately high energy defibrillation is effected by the defibrillator 58 which is correspondingly controlled by pacemaker 10.

Instead of programming pacemaker 10 by the programming device 42 connected to the skin acoustic transducer, or in addition thereto, programming of pacemaker 10, in conformity with FIG. 4, likewise can be effected through the telephone circuit by means of a simple auxiliary device in form of a modem 66. Modem 66 includes an acoustic body bus receiver 68 and a body bus transmitter 69 (or a single transceiver 34 or 27 as shown in external programmer 42 and pacemaker 10) which, in turn, are connected to external skin transducer 70. By a corresponding software design, pacemaker 10 at first can test, with the aid of test signals, the data transport rate of the used telephone network to subsequently automatically adjust the acoustic ultrasound body bus transmitter 69 to the data rate adapted to be communicated.

It is possible to make sure that all data are communicated through the acoustic body bus and that, therefore, the intracardiac ECG can be encoded acoustically and transmitted by modulated ultrasound waves. Similarly all data which occurs in pacemaker 10 can be communicated acoustically through the telephone circuit. Data monitoring and keeping of data archives likewise is possible. Thus, in view of the fact that a medium frequency range is used, a tape recorder 72 can be connected to the acoustic transducer 40, or 70 in order to record the body bus signals which subsequently can be centrally evaluated by a processor or computer.

Figure 5:
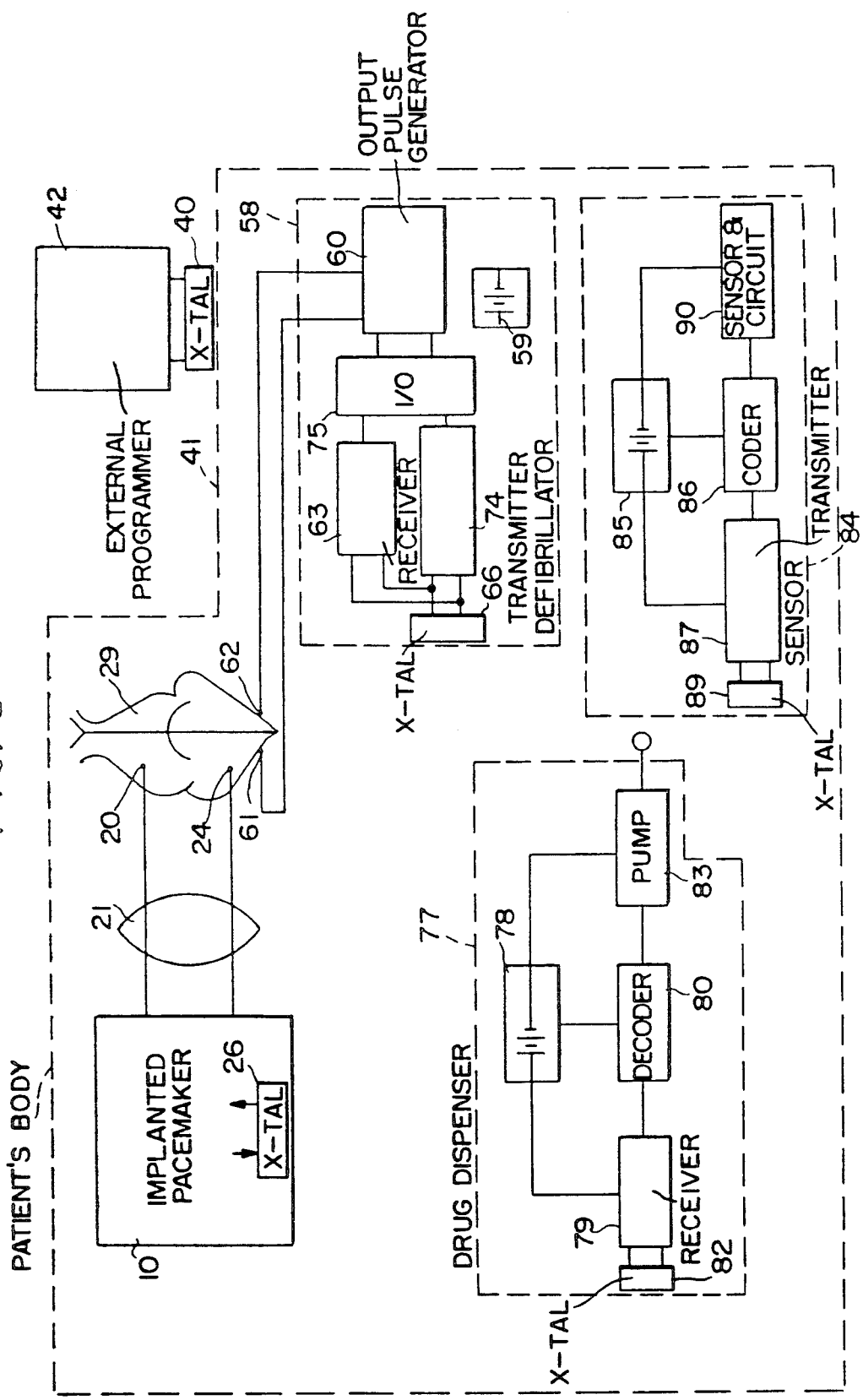

FIG. 5 illustrates a further embodiment in which the defibrillator 58, too, bidirectionally receives and delivers data. For this purpose, an acoustic body bus transmitter 74 coupled to a piezoelectric transducer 66 is provided in addition to the body bus receiver 63 coupled to the transducer. Transmitter 74 and receiver 63 are connected to an input/output unit 75 which provides for the necessary coding and decoding of the signals applied to and received from the piezoelectric transducer 66. Such a design allows more complicated software structures of the defibrillation protocol. For example, the pacemaker 10, in case of an impending fibrillation, as a precaution, can request the defibrillator 58 to make available a shock which is not delivered to the body until the defibrillator 58 informs the pacemaker that the shock energy is ready. The pacemaker, in response to further monitoring of the heart activity, can decide whether or not the shock is to be delivered to the heart. When the shock, made ready as a precaution, is not required, the pacemaker 10 can deliver a corresponding command to the defibrillator 58, which command causes that the storage capacitor of the defibrillator is slowly discharged or that the energy stored in the storage capacitor is returned through a converter into the defibrillator battery 59, which in this case is rechargeable, in order to save energy. It is also possible that the pacemaker 10 applies possibly dangerous antitachycardiac stimulation modes not before it has made sure through the ultrasound body bus that in case of an emergency the shock immediately will be available.

FIG. 5 further schematically illustrates an implantable drug delivery device 77 including a battery 78, an ultrasound body bus receiver 79, a transducer 82, a decoder 80 and a drug pump 83. The casing of the device forms a first electrode 81 connected to one side of the transducer 82 and an input of the receiver 79, whereas a further side of the transducer 82 is connected to a second input of receiver 79. Piezoelectric transducer 82 can receive, through the ultrasound body bus, instructions from pacemaker 10 to the drug delivery device 77 to deliver a bolus of a drug. Device 77, in a manner similar to defibrillator 58 of FIG. 5, likewise can be designed for a bidirectional exchange of information to allow replies to the pacemaker 10.

FIG. 5 finally illustrates a remote physiologic sensor 84 included in the ultrasound body bus system, which sensor comprises a battery 85, a coder 86, a body bus transmitter 87, a sensor and its associated circuitry 90 and the piezoelectric crystal 89. An output of the body bus transmitter 87 is connected to a first electrode 88 defined by the sensor casing, whereas a second input of the body bus transmitter 87 is connected to the crystal transducer 89. The sensor 89, in a manner known per se, is adapted to sense respiration body activity or body parameters such as arterial blood pressure, temperature, pH value, $pO_2$ value and the like. Corresponding signals are telemetered to the pacemaker 10 through the ultrasound body bus for suitably influencing the pacemaker. For example, the sensor data may be used to confirm the existence and nature of a bradyarrhythmia or tachyarrhythmia to influence the selection of the therapy by the pacemaker, drug dispenser or defibrillator and to influence the rate of bradyarrhythmia pacing. The sensor likewise can be designed for a bidirectional exchange of data. In this case it e.g. will be possible to let the pacemaker 10 control sensor characteristics such as the sensitivity of the sensor.

It is evident that the invention can be further modified in many different ways. For example, it is possible to at first implant an AAI pacemaker provided with body bus characteristics. If later on an AV block requires ventricular stimulation, a VVI pacemaker with body bus may be additionally, e.g. myocardially, implanted. The VVI pacemaker and the AAI pacemaker, by exchanging information therebetween, can cooperate to provide for a DDD function.

A further possible application is the implantation of a pacemaker having dP/dt functions for controlling pacing rate as a function of blood pressure rate of change. In such a case, information for delivering from a simultaneously implanted drug delivery device a drug influencing the blood pressure can be transmitted through the body bus. Thereby a "closed loop" system for blood pressure control is realized.

It is apparent that in each case suitable protocols for the data transmission, for securing priorities, for providing for redundancy and the like, are to be used.

The body bus receivers likewise, in a manner known per se, may be provided with an automatic gain control (AGC).

Figure 6:
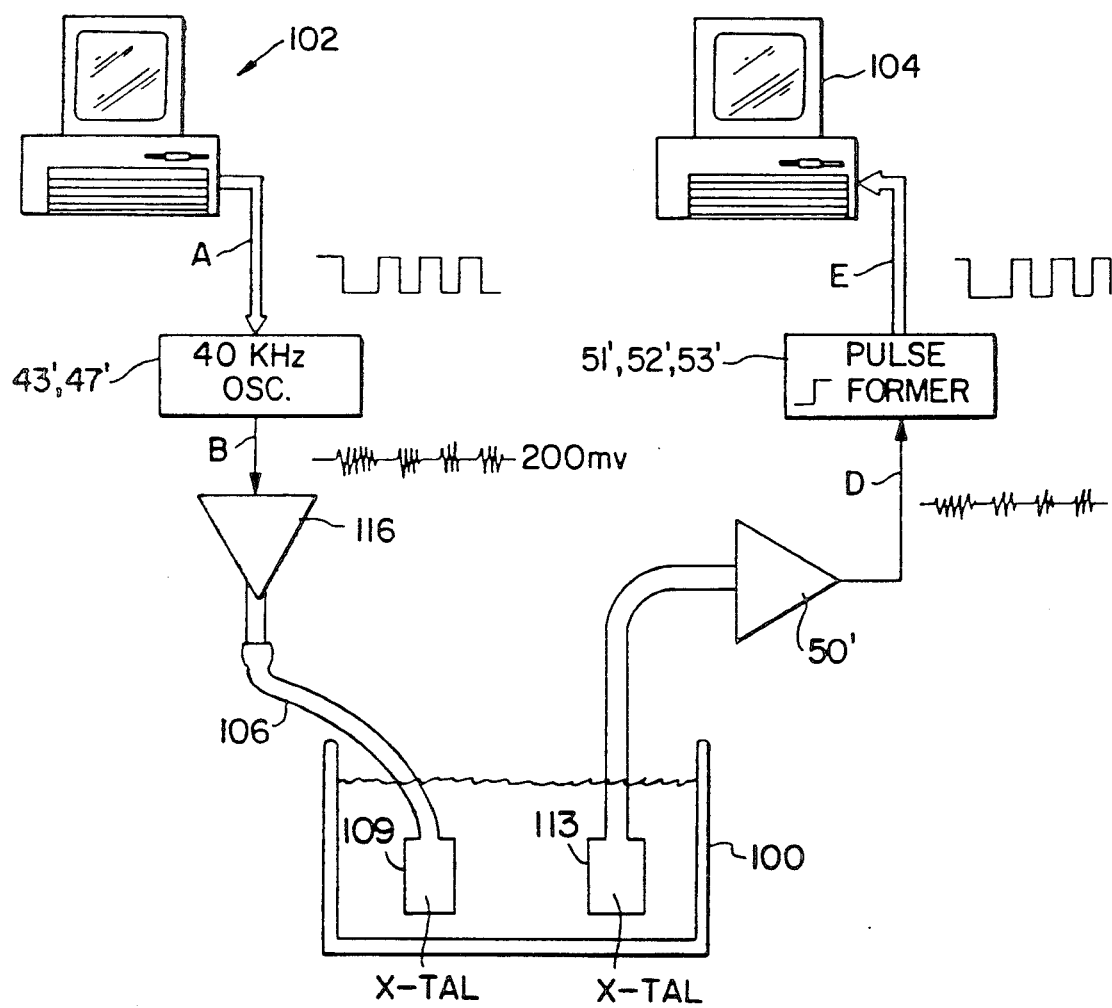
FIG. 6 illustrates the experimental setup prepared to demonstrate ultrasound body bus signal transmission.

An experimental setup prepared by the inventor to test the practicality of the acoustic ultrasound body bus communication system proposed above is illustrated in FIG. 6 and comprises a physiologic saline test tank 100, two personal computers 102 and 104, a first lead 106 having a pair of conductors coupled to electrodes on each side of a planar piezoelectric crystal 109 located within the saline solution, a second pair of conductors coupled to electrodes on each side of a second planar piezoelectric crystal 113 likewise located within the solution, and transmitting and receiving interconnecting circuitry. The transmitting computer 102 is coupled to the proximal terminals of the lead 106 by the crystal oscillator 43', 47' corresponding to the transmitter circuit of FIG. 2. Similarly, the transducer 113 is coupled to the input of preamplifier 50', the output of which is coupled to the pulse former circuitry 51', 52', 53' which collectively correspond to the receiver circuit of FIG. 3. The output signal of the pulse former 51', 52', 53' is applied to the second personal computer 104.

Commercially available, low cost telecontrol piezoelectric transducers were obtained and placed apart a distance approximating the distance that separate devices would normally be spaced in actual implantations in patients. The acoustic ultrasound transducers were placed so that their crystal surfaces faced one another. The tank 100 was filled with physiological saline solution. The experiments were conducted to test the hypothesis that useful information could be transmitted acoustically in both directions through the conducting medium between the tranducers 109 and 113.

With the 8032 model Commodore personal computer, text was entered by its keyboard which is converted into the corresponding ASCII-NR. code which is written as an 8-bit byte into a memory location. This byte is then converted into a serial train of bit pulses preceded by a leader pulse and is emitted from its cassette port so as to gate the output of the signal generator 43', 47' at 40 kHz. With an appropriate level (5 volts) these 40 kHz burst pulses are fed to the first hermetically sealed transducer 109 immersed in the physiologic saline solution. The signals are shown illustrated at points A and B in FIG. 6, the leader illustrated as the initial wide burst signal. A1 Pulse modulation was employed to encode the stream of bits emitted by the transducer 109 into the saline solution.

The signals emitted from the transducer 109 travel through the saline solution and are picked up by the second transducer 113 and applied to the input terminals of preamplifier 50'. The signal level at the input terminals of amplifier 50' is approximately 1 mV at 15 cm distance. After filtering and amplification by the amplifier 50' and pulse former 51', 52', 53', the lower edge envelope curve is reconstructed so that at this stage, the serial 8 bit pulse train with its leader can be applied to an input port or user port of a second 8032 Commodore personal computer. After serial to parallel conversion, the received code is displayed on the computer screen.

Various experiments were conducted with the orientation of the transducer 109, 113 wherein it was found that the only orientation that became insufficient was when the transmitting acoustic wave provided by the transducer 109 was directly perpendicular to the planar surface of the transducer 113 (or conversely). A computer listing actually used to transmit the statement "the quick brown fox jumps over the lazy dog" between the transmitting and the receiving personal computers is attached hereto as follows:

```
     pulses are fed to the first hermetically sealed transducer
     109 immersed in the physiologic saline solution.  The
     signals are shown illustrated at points A and B in Fig. 6,
     the leader illustrated as the initial wide burst signal.
     A1 Pulse modulation was employed to encode the stream of
     bits emitted by the transducer 109 into the saline
     solution.

The signals emitted from the transducer 109 travel
     through the saline solution and are picked up by the
     second transducer 113 and applied to the input terminals
     of preamplifier 50'.  The signal level at the input
     terminals of amplifier 50' is approximately 1 mV at 15 cm
     distance.  After filtering and amplification by the
     amplifier 50' and pulse former 51', 52', 53', the lower
     edge envelope curve is reconstructed so that at this
     stage, the serial 8 bit pulse train with its leader can be
     applied to an input port or user port of a second 8032
     Commodore personal computer.  After serial to parallel
     conversion, the received code is displayed on the computer
     screen.

Various experiments were conducted with the
     orientation of the transducer 109, 113 wherein it was
``` found that the only orientation that became insufficient was when the transmitting acoustic wave provided by the transducer 109 was directly perpendicular to the planar surface of the transducer 113 (or conversely). A computer listing actually used to transmit the statement "the quick brown fox jumps over the lazy dog" between the transmitting and the receiving personal computers is attached hereto as follows:

START OF TRANSMITTER ( BASIC)

```
100 rem name of program:  12b transmit.
105 rem purpose: transmitting ascii code for bodybus.
110 rem principle:  parallel to serial conversion ('lsr')
115 rem              and keying of a 40 khz oscillator thru
120 rem              cassette port #2 of a commodore
                     computer.
125 rem              the oscillator output (bursts, 40 khz,
130 rem              5V) is conducted into .9% saline
135 rem              by a 40 khz telecontrol crystal.
140 if peek (19999)<>17then poke 19999,17:load"12m
    transmit",8,1
145 poke 20006,12:poke20029,3:poke20037,6:poke20093,3:rem
    increments in 1ms
150 sys63739:poke59456,227:rem initializing cassette port
    #2 for transmission
155 y$="_____The quick brown fox jumps over the lazy dog
    1 2 3 4 5 6 7 8 9 0"
160 fora=1to68:b$=mid$(y$,a,1):gosub185:nexta:print
165 b=13:gosub190
170 print"More code entered by keyboard.":print
175 getb$:lfb$=""then175:rem get input from keyboard
180 gosub185:goto175
185 b=asc(b$)
190 printchr$(b);:poke20003,b:sys20004:return:rem transmit
    ascii-#
```

END OF TRANSMITTER (BASIC)

START OF TRANSMITTER (ASSEMBLY 6502)

```
20000 nop
20001 nop
```

```
20002 nop
20003 brk
20004 sei
20005 lda      12
20007 stam  20055
20010 jsr   20054
20013 jsr   20092
20016 ldx       8
20018 ldam  20003
20021 clc
20022 lsr
20023 stam  20003
20026 bcs   20036
20028 lda       3
20030 stam  20055
20033 jmp   20041
20036 lda       6
20038 stam  20055
20041 jsr   20054
20044 jsr   20092
20047 dex
20048 bne   20018
20050 cli
20051 rts
20052 brk
20053 brk
20054 lda       3
20056 stam  20052
20059 lda     243
20061 stam  59456
20064 lda      75
20066 stam  20053
20069 decm  20053
20072 nop
20073 nop
20074 bne   20069
20076 decm  20052
20079 bne   20064
20081 lda     227
20083 stam  59456
```

```
20086 rts
20087 nop
20088 nop
20089 nop
20090 brk
20091 brk
20092 lda     3
20094 stam 20090
20097 lda     75
20099 stam 20091
20102 decm 20091
20105 nop
20106 nop
20107 bne  20102
20109 decm 20090
20112 bne  20097
20114 rts
```
END OF TRANSMITTER (ASSEMBLY 6502)

START OF RECEIVER (BASIC)
```
100 rem name of program:  12b receiver
105 rem purpose:    receive and decode ascii code for
110 rem principle:  bodybus amplification, filtering,
111 rem             pulse forming and decoding ('ror').
112 rem             The signals (bursts, 40 khz, .6mV) are
113 rem             received through a 40 khz crystal
114 rem             immersed in .9% saline.
115 ifpeek(19999)<>17thenpoke19999,17:load"12m receiver",8,1
120 poke20016,8:poke20087,4:rem speed intervals in ms
125 sys20000:rem start of 12m receiver
130 printchr$(peek(20063));:rem print received character
    on screen
135 go to 125
```
END OF RECEIVER (BASIC)

START OF RECEIVER (ASSEMBLY 6502)
```
20000 sei
20001 lda     1
20003 bitm 59471
20006 bne  20001
20008 jmp  20015
20011 nop
20012 nop
```

```
20013 brk                    20077 bne    20074
20014 brk                    20079 lda       1
20015 lda       8            20081 bitm 59471
20017 stam 20013             20084 bne    20079
20020 lda      75            20086 lda       ?
20022 stam 20014             20088 stam 20064
20025 lda       1            20091 lda      57
20027 bitm 59471             20093 stam 20065
20030 bne    20045           20096 lda       1
20032 decm 20014             20098 bitm 59471
20035 bne    20025           20101 bne    20116
20037 decm 20013             20103 decm 20065
20040 bne    20020           20106 bne    20096
20042 jmp    20050           20108 decm 20064
20045 cli                    20111 bne    20091
20046 rts                    20113 jmp    20127
20047 nop                    20116 clc
20048 nop                    20117 ldam 20063
20049 nop                    20120 ror
20050 lda                    20121 stam 20063
20052 bitm 59471             20124 jmp    20142
20055 beq    20050           20127 sec
20057 jmp    20067           20128 ldam 20063
20060 nop                    20131 ror
20061 nop                    20132 stam 20063
20062 nop                    20135 lda       1
20063 oram 10753             20137 bitm 59471
20066 brk                    20140 beq    20135
20067 ldx       8            20131 dex
20069 lda     255            20143 bne    20069
20071 stam 20066             20145 cli
20074 decm 20066             20146 rts
```

<u>END OF RECEIVER (ASSEMBLY 6502)</u>

The above program is the same program that appears in my commonly assigned, copending U.S. Patent Application Serial No. 07/408,811 and contains only slightly changed explanatory comments as to its use with acoustic crystals rather than the electrodes and opto-couplers employed in the '811 application. Thus the same program was employed with higher voltage pulses (0.5 - 5.0 volts) and a 40kHz frequency.

The above program is the same program that appears in my commonly assigned, copending U.S. patent application Ser. No. 07/408,811 and contains only slightly changed explanatory comments as to its use with acoustic crystals rather than the electrodes and opto-couplers employed in the '811 application. Thus the same program was employed with higher voltage pulses (0.5–5.0 volts) and a 40 kHz frequency.

From the foregoing description, it will be apparent that the ultrasound body bus system of the present invention has a number of advantages, some of which have been described above and others of which are inherent in the invention. Also it will be apparent that modifications can be made to the system without departing from the teachings of the present invention. Accordingly, the scope of the invention is only to be limited as necessitated by the accompanying claims.

What is claimed is:

1. A system for providing pacing, cardioversion and defibrillation staged therapies for bradycardia, tachycardia and fibrillation of a patient's heart, comprising:
   (A) a body implantable pacemaker comprising:
      (1) pacing energy pulse generator means for applying pacing stimuli to said heart;
      (2) pacing lead means bearing at least one electrode means adapted to be placed in contact with or within said heart and coupled to said pulse generator means for applying said pacing stimuli to said heart and receiving electrical signals appearing at the tissue-electrode interface;
      (3) sensing means coupled to said electrode means for sensing electrical signals appearing at said electrode means;
      (4) detecting means responsive to said sensing means for detecting a bradyarrhythmia, tachyarrhythmia or ventricular fibrillation condition of said heart;
      (5) first control means responsive to said detecting means for instructing said pulse generator means to provide;
         (a) pacing stimuli to said pacing electrode means in response to the detection of a bradyarrhythmia or tacharrhythmia condition; and
         (b) an encoded defibrillation shock control command in response to the detection of a ventricular fibrillation condition, said encoded defibrillation shock command comprising a predetermined modulated first medium frequency signal in the frequency range from 10 to 100 kHz; and
      (6) first acoustic transducer means acoustically coupled to the body fluids and tissue of said patient for transducing said encoded defibrillation shock control command into modulated ultrasonic acoustic waves for transmission into said body fluids and tissue as a function of said modulated first medium frequency signal; and
   (B) a remotely implanted defibrillator comprising:
      (1) defibrillation pulse generator means for generating defibrillation shocks;
      (2) defibrillation electrode means adapted to be placed in contact with said heart for providing defibrillation shocks thereto;
      (3) second acoustic transducer means acoustically coupled to said body fluids and tissue for transducing said modulated ultrasonic acoustic waves transmitted from said pacemaker into said modulated first medium frequency signal;
      (4) receiving means coupled to said second acoustic transducer means for demodulating said modulated first medium frequency signal into a decoded defibrillator shock control command; and
      (5) second control means responsive to said decoded shock control command for instructing said defibrillation pulse generator to provide a defibrillation shock across said defibrillation electrode means as a function of said decoded shock control command.

2. The system according to claim 1 wherein:
   (A) said defibrillator further comprises:
      (1) encoding means for encoding data representative of an operating state of said defibrillator, said encoded defibrillator data comprising a predetermined modulated second medium frequency signal in the frequency range from 10 to 100 kHz; and
      (2) said second acoustic transducer means further comprising means for transducing said encoded defibrillator data signal into modulated ultrasonic acoustic waves for transmission into said body fluids and tissue as a function of said modulated second medium frequency signal;
   (B) said pacemaker further comprises:
      (1) said first acoustic transducer means further comprising means for transducing said modulated ultrasonic acoustic waves transmitted from said defibrillator into said encoded defibrillator data signal; and
      (2) receiving means coupled to said first acoustic transducer means for demodulating said modulated second medium frequency signal into said decoded defibrillator data.

3. The system according to claim 2 wherein said first control means of said pacemaker controls said pulse generator means as a function of said decoded defibrillator data.

* * * * *